United States Patent [19]

Truthan

[11] Patent Number: 5,674,195
[45] Date of Patent: Oct. 7, 1997

[54] SYRINGE APPARATUS AND METHOD OF MIXING LIQUID MEDICANTS WITHIN A SYRINGE

[76] Inventor: Charles Edwin Truthan, 4075 Rum Run Ave. SE., Grand Rapids, Mich. 49546

[21] Appl. No.: 383,909

[22] Filed: Feb. 6, 1995

[51] Int. Cl.$^6$ ................................................ A61M 37/00
[52] U.S. Cl. .................. 604/87; 604/56; 604/82; 604/187
[58] Field of Search ................. 604/46, 51, 56, 604/68, 70, 82, 83, 85–91, 118, 87, 192, 210, 218, 228, 236, 240, 241, 243, 247, 905

[56] References Cited

U.S. PATENT DOCUMENTS

| | | | |
|---|---|---|---|
| 554,614 | 2/1896 | Beyer | 604/236 |
| 701,671 | 6/1902 | Billings | 604/218 |
| 2,999,499 | 9/1961 | Willet | 604/83 |
| 3,052,240 | 9/1962 | Silver et al. | 604/89 |
| 3,342,179 | 9/1967 | Ellmann | 604/905 |
| 3,464,412 | 9/1969 | Schwartz | 604/89 |
| 4,581,015 | 4/1986 | Alfano | 604/88 |
| 4,655,214 | 4/1987 | Linder | 128/207.18 |
| 4,685,910 | 8/1987 | Schweizer | 604/218 |
| 4,958,622 | 9/1990 | Selenke | 604/192 |
| 5,032,117 | 7/1991 | Motta | 604/88 |
| 5,045,065 | 9/1991 | Raulerson | 604/167 |
| 5,181,909 | 1/1993 | McFarlane | 604/52 |
| 5,188,594 | 2/1993 | Zilberstein | 604/51 |

*Primary Examiner*—Corrine M. McDermott
*Assistant Examiner*—N. Kent Gring
*Attorney, Agent, or Firm*—Van Dyke, Gardner, Linn & Burkhart, LLP

[57] ABSTRACT

A syringe apparatus (10) comprising: a syringe barrel (12), a plunger apparatus (11) with, resealable injection port (18) thru which multiple syringes with needle prefilled with intraveinous medication are injected into syringe chamber (22) which is prefilled with a diluent. The medications are mixed to the appropriate endotracheal administration concentration and volume, then discharged through discharge valve assembly (26) comprising a one-way valve (28) and twist lock discharge port (30). Syringe apparatus (10) is connected to an endotracheal tube with needleless medication injection port, or other device, and the medication is forcefully expelled to the respiratory passageways and absorbed by the pulmonary vasculature. Syringe apparatus (10) can mix medications from needleless syringes by attachment to double female adaptor apparatus (34). Syringe apparatus (10) can be used to mix any liquid medicants that need to be injected into any device that requires administration by a syringe.

25 Claims, 1 Drawing Sheet

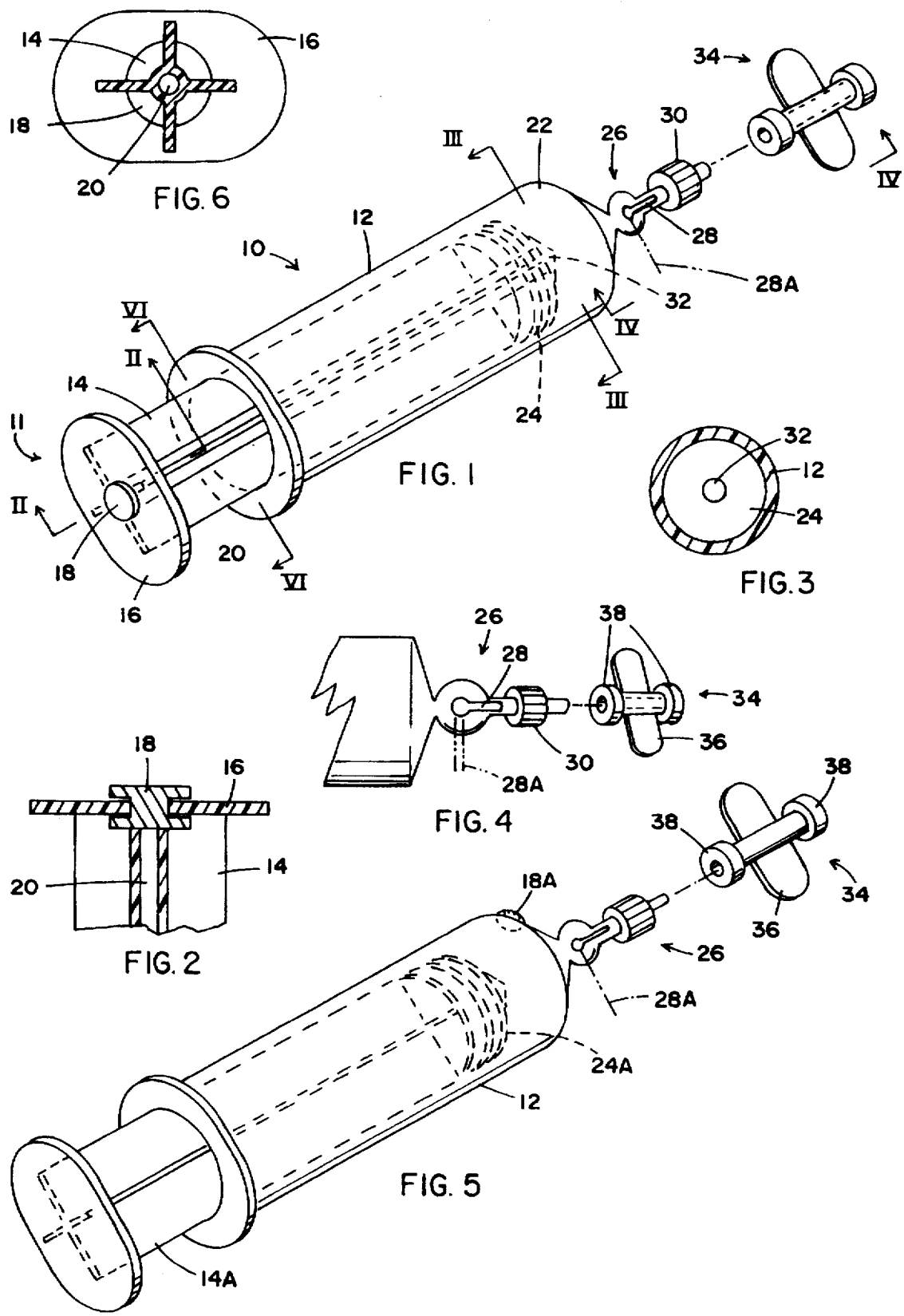

SYRINGE APPARATUS AND METHOD OF MIXING LIQUID MEDICANTS WITHIN A SYRINGE

CROSS REFERENCES TO RELATED APPLICATIONS

The invention of this application is related to my invention ENDOTRACHEAL TUBE WITH NEEDLELESS MEDICATION INJECTION PORT.

The invention of this application is related to my invention ENDOTRACHEAL TUBE INSERT WITH NEEDLELESS MEDICATION INJECTION PORT.

1. Background—Field of Invention

The invention relates to the field of medicine, specifically to a syringe capable of mixing liquid medicants from prefilled syringes with needles and then rapidly delivering them to a patient.

2. Background—Description of Prior Art

In medical emergencies, the rapid administration of medicines is usually accomplished via the intraveinous route. When this route is not available, the only alternative is to administer the medications via the pulmonary vasculature to the systemic vasculature. This is accomplished currently by administering the intraveinous medication directly into an endotracheal tube's proximal end or by passing a small catheter down the endotracheal tube and administering the intraveinous medication down the catheter.

Current medical recomendations require the administration of two to two and one-half times the doseage of intraveinous medication for the endotracheal route. Further, this higher dose is to be diluted in ten cc. of normal saline or sterile water.

Currently, emergency medications are premixed and preloaded in syringes with needles for intraveinous injection. In order to mix the recomended dosages, it is necessary to empty the syringes into a sterile container, add the saline or sterile water and then redraw this mixture up into a syringe and then administer it. In the worse case, the intraveinous medication is administered directly into the endotracheal tube undiluted.

U.S. Pat. No. 5,298,024 to Richmond, Frank (Mar. 29, 1994), is designed to carry preloaded medicants stored separately within a syringe and administered sequentially. It does not allow for the drawing up of liquid medicants from a separate preloaded syringe.

U.S. Pat. No. 4,613,326 to Szware, Joseph (Sep. 23, 1986), is designed to carry preloaded medicants stored separately and mixed just prior to injection. It does not allow for the drawing up of liquid medicants from a separate preloaded syringe.

U.S. Pat. No. 4,976,696 to Sanderson, George; Strowe, Robert J. (Dec. 11, 1990), is a pump to squeeze the syringe after it is filled with liquid medicant.

None of the aforementioned inventions is a syringe that allows for the direct mixing of liquid medicants from separate preloaded syringes and then the administration of the new mixture into the body.

OBJECTS AND ADVANTAGES

Accordingly, several objects and advantages of my invention are the direct mixing of (intraveinous) medications from separate preloaded syringes into the syringe of this invention, that is then capable of immediately passing the diluted medication in the proper doseage into the body (e.g. via an endotracheal tube). When this syringe is preloaded with ten cc of diluent (normal saline or sterile water) one additional step is eliminated and time is saved during the (emergency) administration procedure. Further, when this invention is used in conjunction with a needleless endotracheal tube medication administration device, the risk for accidental needle stick to the patient or to medical personnel is eliminated.

With a minimal consumption of space, this syringe can be added to Emergency rooms and Paramedic ambulance services while still allowing them to carry their current preloaded syringe intraveinous dosing forms.

Still further objects and advantages will become apparent from a consideration of the ensuing description and accompanying drawings.

BRIEF DESCRIPTION OF THE DRAWINGS

FIG. 1 is a perspective view of my invention.

FIG. 2 is a longitudinal-section view in detail of the portion indicated by section lines 2—2 in FIG. 1.

FIG. 3 is a cross-section view in detail of the portion indicated by section lines 3—3 in FIG. 1.

FIG. 4 is a view in detail of the portion indicated by section lines 4—4 in FIG. 1.

FIG. 5 is a perspective view of one alternative injection port location.

FIG. 6 is a cross-section view in detail of the portion indicated by section lines 6—6 of FIG. 1.

REFERENCE NUMERALS 10 syringe apparatus
11 plunger apparatus
12 syringe barrel
14 plunger
14A plunger
16 plunger handle
18 resealable injection port
18A resealable injection port
20 central passage
22 syringe chamber
24 plunger barrel occluder
24A plunger barrel occluder
26 discharge valve assembly
28 one-way valve
28A one-way valve
30 twist lock discharge port
32 barrel occluder opening
34 double female adaptor apparatus
36 gripwing
38 female end

SUMMARY

A syringe apparatus that allows for the rapid mixing of intraveinous medications from syringes, with or without a needle, that are prefilled with liquid medicants, mixed to appropriate concentration and then injected into the respiratory system via an endotracheal tube or other device and absorbed into the bloodstream of a patient.

PREFERRED EMBODIMENT—DESCRIPTION

FIG. 1 shows a perspective view of my syringe apparatus 10. At one end of syringe barrel 12 is a plunger apparatus 11, consisting of a plunger 14 with a central passage 20. In the plunger handle 16 is a resealable injection port 18 which connects to central passage 20 of plunger 14. Central passage 20 opens into syringe chamber 22 by passing thru plunger barrel occluder 24 at barrel occluder opening 32. At the other end of syringe apparatus 10 is the discharge valve assembly 26, consisting of one-way valve 28, a twist lock discharge port 30, and a double female adaptor apparatus 34.

FIG. 2 is a longitudinal-section view in detail of the portion indicated by section lines 2—2 in FIG. 1. It shows the resealable injection port 18 connected thru plunger handle 16 connecting to central passage 20 of plunger 14.

FIG. 3 is a cross-section view in detail of the portion indicated by section lines 3—3 in FIG. 1. It shows the plunger barrel occluder 24 within the syringe barrel 12 with barrel occluder opening 32.

FIG. 4 is a view in detail of the portion indicated by section lines 4—4 in FIG. 1. It shows the discharge valve assembly 26 with the one-way valve 28 in the open position and one-way valve 28A in the closed position, with twist lock discharge port 30 downstream. A double female adaptor apparatus 34 is detachable from twist lock discharge port 30 and allows for the connection of a syringe without a needle. The double female adaptor apparatus 34 consists of a gripwing 36 and two female ends 38 that are capable of twist locking into twist lock discharge port 30.

FIG. 5 is a perspective view of one alternative injection port location. Resealable injection port 18A is located on the discharge end of syringe barrel 12 opposite one-way valve 28's area needed for operation. Plunger apparatus 11 does not need to be of a hollow core style. Plunger barrel occluder 24A does not have a barrel occluder opening 32.

FIG. 6 is a cross-section view in detail of the portion indicated by section lines 6—6 in FIG. 1. It shows plunger 14 with central passage 20, plunger handle 16, and resealable injection port 18.

PREFERRED EMBODIMENT—OPERATION

A syringe and needle prefilled with medication for intraveinous administration is injected into syringe apparatus 10 at resealable injection port 18 in plunger handle 16 of plunger apparatus 11 while discharge valve assembly 26 has one-way valve 28A in the closed position. The medication is passed thru central passage 20 of plunger 14, thru barrel occluder opening 32 and into syringe chamber 22. Additional prefilled syringes may be added until appropriate doseage for endotracheal administration has been reached (usually two to two and one-half times the intraveinous doseage). The syringe apparatus 10 is prefilled with diluent (10 cc. of normal saline or sterile water) and is now ready for injection into a needleless medication injection port of the endotracheal tube. The twist lock discharge port 30 is connected to the needleless medication injection port of the endotracheal tube, one-way valve 28 is moved to the open position, force is applied on plunger handle 16 causing the medicant within syringe chamber 22 to be forcefully expelled thru discharge valve assembly 26 and into the needleless medication injection port of the endotracheal tube and hence into the lungs of the patient and absorbed into the bloodstream of the patient.

With the double female adaptor apparatus 34 attached by one female end 38 to the twist lock discharge port 30 of syringe apparatus 10, it is possible to connect a needleless syringe that is prefilled with liquid medicant and by opening one-way valve 28 add that liquid medicant to syringe chamber 22. The gripwing 36 of double female adaptor apparatus 34 allows the operator a place to grip double female adaptor apparatus 34 and easily twist it into or out of twist lock discharge port 30.

If syringe apparatus 10 were not prefilled with diluent, either prior to the injection of the syringe prefilled with medication for intraveinous administration or after the injection of syringe prefilled with medication for intraveinous administration into syringe chamber 22 in adequate amounts for endotracheal administration, a needle is attached to twist lock discharge port 30 and 10 cc of diluent is drawn up by opening one-way valve 28 and applying a negative force to plunger handle 16. The needle is then removed and injected into the needleless medication injection port of the endotracheal tube as described before.

if there is no needleless medication injection port for the endotracheal tube but rather a needle is required, one can be attached to twist lock discharge port 30 and the diluted medication injected as described above.

In one variation of syringe apparatus 10, the resealable injection port 18A is located on the discharge end of syringe barrel 12, adjacent to discharge valve assembly 26, but opposite the area for operating one-way valve 28 of discharge valve assembly 26. Plunger barrel occluder 24A is formed without barrel occluder opening 32 and plunger 14A does not need to be of a hollow tubular design. A syringe prefilled with medication for intraveinous administration is injected thru resealable injection port 18A directly into syringe chamber 22.

it is to be understood that applicant's invention in not limited to administration only thru a dedicated medication port of an endotracheal tube but can also be used directly down the endotracheal tube or a small catheter passed down an endotracheal tube. Further, it is to be understood that applicant's invention in not limited to administration of medications thru an endotracheal tube, but can be used on any apparatus that requires the mixing and dispensing of liquid medicants thru a syringe type mechanism. For example, a syringe pump for administering mixed medication used for disolving blood clots in the heart or elsewhere in the body. Another example is forcing mixed medications thru a colonoscope, bronchosope or other similar instrument.

Conclusions, Ramifications, and Scope

Accordingly, it can be seen that syringe apparatus 10 allows for the mixing of medications within syringe chamber 22 by the insertion of the needle of a syringe containing liquid medicants thru resealable injection port 18. It further allows for the mixing of medications within syringe chamber 22 by the attachment of a syringe containing liquid medicants without a needle at double female adaptor apparatus 34. This allows emergency medical personnel to utilize existing premixed intraveinous doseage syringe systems and dilute them to appropriate endotracheal concentration, then directly administer them, thereby eliminating an administration step and shortening the time delay in which emergency medications can be delivered to the patient. When used with an endotracheal tube with needleless medication injection port, or with a small catheter passed down an endotracheal tube, the risk of accidental needle stick to the patient and to medical personnel is eliminated. Syringe apparatus 10 is capable of attaching a needle for injection of or drawing up of liquid medicants.

Although the description above contains many specificities, these should not be construed as limiting the scope of the invention but as merely providing illustrations of some of the presently preferred embodiments of this invention. Various other embodiments and ramifications are possible within it's scope. For example, syringe apparatus 10 can be used any time medications need to be mixed and administered via a single syringe. Syringe apparatus 10 can be used to administer medication to any apparatus that requires the mixing and dispensing of liquid medicants thru a syringe type mechanism.

Thus the scope of the invention should be determined by the appended claims and their legal equivalents, rather than by the examples given.

What is claimed is:

1. A syringe apparatus capable of receiving liquid medicants from other syringes with needles and is comprised of:

a generally elongated tubular member defining a syringe chamber for mixing of medicants;

said syringe chamber having an open end through which a plunger apparatus enters;

said plunger apparatus including a plunger being of a generally elongated, rigid, tubular member having a resealable injection port in a plunger handle at one end of said plunger and a central passage thru said plunger from said resealable injection port to a plunger barrel occluder at the other end of said plunger, said plunger barrel occluder sliding within said syringe chamber, said central passage passing thru said plunger barrel occluder at a barrel occluder opening and into said syringe chamber;

said syringe chamber further having a smaller opening at the opposite end to which is connected a discharge valve assembly;

said discharge valve assembly having a valve and discharge port;

whereby, with said valve in the closed position, said syringe with needle and said liquid medicant is injected through said resealable injection port in said plunger handle and down said central passage of said plunger through said plunger barrel occluder and through said barrel occluder opening and into said syringe chamber where said liquid medicant is mixed with a diluent until proper concentration of said liquid medicant is attained whereupon the valve is opened and a positive pumping action is effected upon said plunger handle and said plunger forcefully expelling said liquid medicants through said discharge valve assembly.

2. A syringe apparatus set forth in claim 1 wherein said syringe chamber contains diluent.

3. A syringe apparatus set forth in claim 1 wherein said syringe chamber contains a liquid medicant.

4. A syringe apparatus set forth in claim 1 wherein said discharge valve assembly has a nonlocking discharge port.

5. A syringe apparatus as set forth in claim 1 wherein said syringe apparatus includes a needle connected with said discharge port for passing liquid medicants to the lungs or other body part.

6. A syringe apparatus set forth in claim 1 including a detachable double female adaptor apparatus, said double female adaptor apparatus having a gripwing and two female ends, one said female end attaching to said discharge port to which a syringe without needle can be attached at the opposite end of said double female adaptor apparatus and liquid medicant added through said double female adaptor apparatus to said syringe chamber with said valve in the open position.

7. The syringe apparatus as set forth in claim 1 wherein said discharge port includes a twist lock connector.

8. A method of mixing liquid medicants within a single syringe for the delivery of said liquid medicants to a patient comprising:

providing a syringe apparatus having a generally elongated tubular assembly defining a syringe chamber, said assembly includes a discharge valve assembly with a valve and a discharge port at one end, a plunger and a resealable injection port into said syringe chamber;

inserting a needle of a syringe containing liquid medicants into said resealable injection port with said valve in the closed position, and injecting said medicants into said syringe chamber;

upon reaching desired concentration of said liquid medicants, connecting said syringe apparatus to a device for introducing said liquid medicants into said patient at said discharge port, opening said valve and effecting a pumping action on said plunger handle forcefully expelling said liquid medicants into said device.

9. A method of mixing liquid medicants as set forth in claim 8 including prefilling said syringe chamber with liquid diluent.

10. A method of mixing liquid medicants as set forth in claim 8 wherein said syringe apparatus wherein said resealable injection port is located on said tubular assembly.

11. A method of mixing liquid medicants as set forth in claim 8 wherein said syringe apparatus includes a double female adaptor apparatus comprised of a gripwing and two female ends which is attachable and detachable from said discharge port whereby with said valve in the open position, a needleless syringe containing liquid medicants attached to one end of said double female adaptor apparatus can be injected into said syringe chamber through said discharge valve assembly.

12. A method of mixing liquid medicants as set forth in claim 8 wherein said plunger includes a central passage, a plunger barrel occluder and an opening from said center passage through said plunger barrel occluder, wherein said resealable injection port is in said plunger extending into said central passage.

13. The method of mixing liquid medicants as set forth in claim 8 wherein said discharge port includes a twist lock connector.

14. The method of mixing liquid medicants as set forth in claim 8 including attaching a double female adaptor having two female ends to said discharge port and to a needleless injection port of a device.

15. The method of mixing liquid medicants as set forth in claim 14 wherein said device is one of an endotracheal tube, a colonoscope and a bronchoscope.

16. A syringe apparatus adapted to be connected with a device and capable of receiving liquid medicants from other syringes with needles, comprising:

a generally elongated tubular member defining a syringe chamber for mixing medicants;

said syringe chamber having an open end;

a plunger being of a generally elongated, rigid, tubular member extending through said open end into said syringe chamber;

said syringe chamber further having a smaller opening at the opposite end which is connected to a discharge valve assembly, said discharge valve assembly having a valve and a discharge port; and a resealable injection port extending into said syringe chamber.

17. The syringe apparatus in claim 16 wherein said injection port extends through a wall of said syringe chamber.

18. A syringe apparatus set forth in claim 17 wherein said syringe chamber contains diluent.

19. A syringe apparatus set forth in claim 17 wherein said discharge valve assembly has a nonlocking discharge port.

20. A syringe apparatus set forth in claim 17 wherein said syringe apparatus includes a needle connected with said discharge port for passing liquid medicants to the lungs or other body part.

21. A syringe apparatus set forth in claim 17 including a detachable double female adaptor apparatus, said double female adaptor apparatus having a gripwing and two female ends, one said female end attaching to said discharge port to which a syringe without needle can be attached at the opposite end of said double female adaptor apparatus and liquid medicant added through said double female adaptor apparatus to said syringe chamber with said valve in the open position.

22. The syringe apparatus in claim 16 wherein said injection port extends through said plunger into said syringe chamber.

23. The syringe apparatus as set forth in claim 16 wherein said discharge port includes a twist lock connector.

24. The syringe apparatus as set forth in claim 16 including a detachable double female adaptor attached to said discharge port and configured to connect with a needleless injection port of a device.

25. The syringe apparatus in claim 24 wherein said device is one of an endotracheal tube, a colonoscope and a bronchoscope.

* * * * *